United States Patent
Houser et al.

(10) Patent No.: US 9,421,062 B2
(45) Date of Patent: Aug. 23, 2016

(54) SURGICAL INSTRUMENT SHAFT WITH RESILIENTLY BIASED COUPLING TO HANDPIECE

(75) Inventors: Kevin L. Houser, Springboro, OH (US); Patrick A. Weizman, Liberty Township, OH (US); Geoffrey S. Strobl, Williamsburg, OH (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1185 days.

(21) Appl. No.: 13/271,364

(22) Filed: Oct. 12, 2011

(65) Prior Publication Data

US 2012/0116389 A1 May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 18/18* (2006.01)
*A61B 18/14* (2006.01)
(Continued)

(52) U.S. Cl.
CPC ..... *A61B 18/1442* (2013.01); *A61B 17/00234* (2013.01); *A61B 17/2812* (2013.01);
(Continued)

(58) Field of Classification Search
CPC .......................... A61B 19/2203; A61B 19/22
USPC .................................. 606/1, 130; 227/175.1
See application file for complete search history.

(56) References Cited

U.S. PATENT DOCUMENTS 1,754,806 A 4/1930 Stevenson
3,297,192 A 1/1967 Swett
(Continued)

FOREIGN PATENT DOCUMENTS

DE 102008051866 10/2010
DE 102009013034 10/2010
(Continued)

OTHER PUBLICATIONS

US Office Action, Non-Final, dated Nov. 7, 2014 for U.S. Appl. No. 13/151,488.
(Continued)

*Primary Examiner* — William Thomson
*Assistant Examiner* — Jeffrey Lipitz
(74) *Attorney, Agent, or Firm* — Frost Brown Todd LLC

(57) ABSTRACT

An ultrasonic surgical instrument includes a reusable handle assembly and a removable and disposable shaft assembly. The handle assembly includes a trigger, a housing having a distal aperture formed in a distal end of the housing, and a drive member in communication with the trigger to actuate the drive member. The shaft assembly includes a proximal shaft portion, a rotator knob having a coupling feature, a transmission assembly extending distally from the proximal shaft portion, and an end effector coupled to the distal end of the transmission assembly. The drive member of the handle assembly is removably coupled to the proximal shaft portion of the shaft assembly. Another version includes a drive member of the handle assembly configured to removably engage a proximal shaft portion of the shaft assembly via a biasing member. Another version includes a waveguide of the transmission assembly non-threadably coupled to a transducer.

20 Claims, 9 Drawing Sheets

(51) Int. Cl.

| | | |
|---|---|---|
| *A61B 17/00* | (2006.01) | |
| *A61B 17/32* | (2006.01) | |
| *A61B 18/00* | (2006.01) | |
| *A61B 18/04* | (2006.01) | |
| *H02J 7/00* | (2006.01) | |
| *A61B 17/28* | (2006.01) | |
| *H01M 2/26* | (2006.01) | |
| *H01M 2/10* | (2006.01) | |
| *A61B 18/12* | (2006.01) | |
| *A61B 17/064* | (2006.01) | |
| *A61B 17/285* | (2006.01) | |
| *A61B 17/29* | (2006.01) | |

(52) U.S. Cl.
CPC ............... *A61B17/320068* (2013.01); *A61B 17/320092* (2013.01); *A61B 18/00* (2013.01); *A61B 18/04* (2013.01); *A61B 18/12* (2013.01); *A61B 18/14* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,871,493 A | 2/1999 | Sjostrom et al. |
| 5,873,873 A | 2/1999 | Smith et al. |
| 5,882,310 A | 3/1999 | Marian, Jr. |
| 5,893,835 A * | 4/1999 | Witt et al. .................. 601/2 |
| 5,893,874 A | 4/1999 | Bourque et al. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francischelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |

(56) References Cited

U.S. PATENT DOCUMENTS

| | | |
|---|---|---|
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 9,044,261 B2 | 6/2015 | Houser |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |

(56) References Cited

U.S. PATENT DOCUMENTS

| | | |
|---|---|---|
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0074336 A1 | 3/2011 | Miller |
| 2011/0077514 A1 | 3/2011 | Ulric et al. |
| 2011/0080134 A1 | 4/2011 | Miller |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0221398 A1 | 9/2011 | Ferber |
| 2011/0224668 A1 | 9/2011 | Johnson et al. |
| 2011/0247952 A1 | 10/2011 | Habach et al. |
| 2011/0288573 A1 | 11/2011 | Yates et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |
| 2013/0118733 A1 | 5/2013 | Kumar |
| 2013/0342962 A1 | 12/2013 | Fletcher et al. |
| 2014/0088739 A1 | 3/2014 | Ellis et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H10-118090 | 5/1998 |
| JP | 2002-186627 | 7/2002 |
| JP | 4602681 | 12/2010 |
| JP | 4836148 | 12/2011 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

US Office Action, Non-Final, dated Nov. 6, 2014 for U.S. Appl. No. 13/151,503.

US Office Action, Notice of Allowance, dated Oct. 28, 2014 for U.S. Appl. No. 13/151,509.

US Office Action, Notice of Allowance, dated Oct. 29, 2014 for U.S. Appl. No. 13/151,512.

US Office Action, Non-Final, dated Oct. 22, 2014 for U.S. Appl. No. 13/274,830.

US Office Action, Non-Final, dated Oct. 23, 2014 for U.S. Appl. No. 13/275,563.

Office Action Non-Final dated Mar. 28, 2014 for U.S. Appl. No. 13/151,471.

Office Action Non Final dated Mar. 18, 2014 for U.S. Appl. No. 13/151,498.

Office Action Non Final dated Jun. 18, 2014 for U.S. Appl. No. 13/151,503.

(56) References Cited

OTHER PUBLICATIONS

Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
International Search Report and Written Opinion dated Jan. 26, 2012for Application No. PCT/US2011/059212.
International Search Report and Written Opinion dated Feb. 2, 2012for Application No. PCT/US2011/059378.
International Search Report dated Feb. 2, 2012for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012for Application No. PCT/US2011/059362.
Communication from International Searching Authority dated Feb. 2, 2012for Application No. PCT/US2011/059222.
Communication from International Searching Authority dated Jan. 24, 2012 for Application No. PCT/US2011/059215.
Communication from International Searching Authority dated Feb. 2, 2012for Application No. PCT/US2011/059378.
Machine Translation of the Abstract of German Application No. DE 102009013034.
Machine Translation of German Application No. DE 102008051866.
US Office Action, Notice of Allowance, dated Nov. 21, 2014 for U.S. Appl. No. 13/151,471.
US Office Action, Notice of Allowance, dated Nov. 21, 2014 for U.S. Appl. No. 13/151,498.
US Office Action, Notice of Allowance, dated Dec. 17, 2014 for U.S. Appl. No. 13/270,667.
US Office Action, Non-Final, dated Dec. 16, 2014 for U.S. Appl. No. 13/270,701.
US Office Action, Notice of Allowance, dated Nov. 28, 2014 for U.S. Appl. No. 13/274,805.
US Office Action, Notice of Allowance, dated Dec. 19, 2014 for U.S. Appl. No. 13/276,745.
US Office Action, Non-Final, dated Dec. 8, 2014 for U.S. Appl. No. 13/277,328.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Non-Final, dated Aug. 14, 2014 for U.S. Appl. No. 13/151,481.
US Office Action, Notice of Allowance, dated Aug. 6, 2014 for U.S. Appl. No. 13/151,498.
US Office Action, Non-Final, dated Jul. 9, 2014 for U.S. Appl. No. 13/151,509.
US Office Action, Restriction Requirement, dated Jul. 11, 2014 for U.S. Appl. No. 13/269,780.
US Office Action, Non-Final, dated Jul. 29, 2014 for U.S. Appl. No. 13/270,667.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Jul. 9, 2014 for U.S. Appl. No. 13/270,684.
US Office Action, Non Final, dated Oct. 9, 2014 for U.S. Appl. No. 13/270,684.
US Office Action, Restriction Requirement, dated Oct. 2, 2013 for U.S. Appl. No. 13/274,480.

(56) References Cited

OTHER PUBLICATIONS

US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.

(56) References Cited

OTHER PUBLICATIONS

Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Australian First Examination Report dated Jun. 11, 2015 for Application No. AU2011323281.
Chinese First Office Action dated Apr. 16, 2015 for Application No. CN201180063919X.
Chinese First Office Action dated Jun. 1, 2015 for Application No. CN2011800640981.
Japanese Notification of Reasons for Refusal dated Aug. 25, 2015 for Application No. 2013-537831.
US Office Action, Final, dated Apr. 1, 2015 for U.S. Appl. No. 13/151,481.
US Office Action, Notice of Allowance, dated Feb. 25, 2015 for U.S. Appl. No. 13/151,509.
US Office Action, Notice of Allowance, dated Feb. 17, 2015 for U.S. Appl. No. 13/151,512.
US Office Action, Non-Final, dated Jan. 5, 2015 for U.S. Appl. No. 13/269,870.
US Office Action, Final, dated Aug. 14, 2015 for U.S. Appl. No. 13/269,870.
US Office Action, Final, dated Mar. 17, 2015 for U.S. Appl. No. 13/270,684.
US Office Action, Notice of Allowance, dated Jul. 28, 2015 for U.S. Appl. No. 13/270,684.
US Office Action, Non-Final, dated Mar. 26, 2015 for U.S. Appl. No. 13/271,352.
US Office Action, Final, dated Jul. 15, 2015 for U.S. Appl. No. 13/271,352.
US Office Action, Non-Final, dated Apr. 2, 2015 for U.S. Appl. No. 13/274,496.
US Office Action, Non-Final, dated Jul. 22, 2015 for U.S. Appl. No. 13/274,507.
US Office Action, Final, dated May 8, 2015 for U.S. Appl. No. 13/274,516.
US Office Action, Notice of Allowance, dated Sep. 24, 2015 for U.S. Appl. No. 13/274,516.
US Office Action, Notice of Allowance, dated Jan. 21, 2015 for U.S. Appl. No. 13/274,540.
US Office Action, Notice of Allowance, dated Jan. 21, 2015 for U.S. Appl. No. 13/274,805.
US Office Action, Notice of Allowance, dated Mar. 23, 2015 for U.S. Appl. No. 13/274,830
US Office Action, Non-Final, dated Feb. 25, 2015 for U.S. Appl. No. 13/275,495.
US Office Action, Final, dated Mar. 10, 2015 for U.S. Appl. No. 13/275,547.
US Office Action, Final, dated Mar. 13, 2015 for U.S. Appl. No. 13/276,673.
US Office Action, Notice of Allowance, dated Dec. 23, 2014 for U.S. Appl. No. 13/276,687.
US Office Action, Non-Final, dated Jan. 29, 2015 for U.S. Appl. No. 13/276,707.
US Office Action, Notice of Allowance, dated Mar. 13, 2015 for U.S. Appl. No. 13/276,725.
US Office Action, Final, dated Mar. 24, 2015 for U.S. Appl. No. 13/277,328.
US Office Action, Notice of Allowance, dated Jun. 1, 2015 for U.S. Appl. No. 13/277,328.
Japanese Office Action, Notification of Reasons for Refusal, dated Sep. 8, 2015 for Application No. 2013-537830.
US Office Action, Notice of Allowance, dated Nov. 30, 2015 for U.S. Appl. No. 13/270,684.
US Office Action, Final, dated Dec. 8, 2015 for U.S. Appl. No. 13/274,507.
US Office Action, Notice of Allowance, dated Feb. 19, 2016 for U.S. Appl. No. 13/271,352.

* cited by examiner

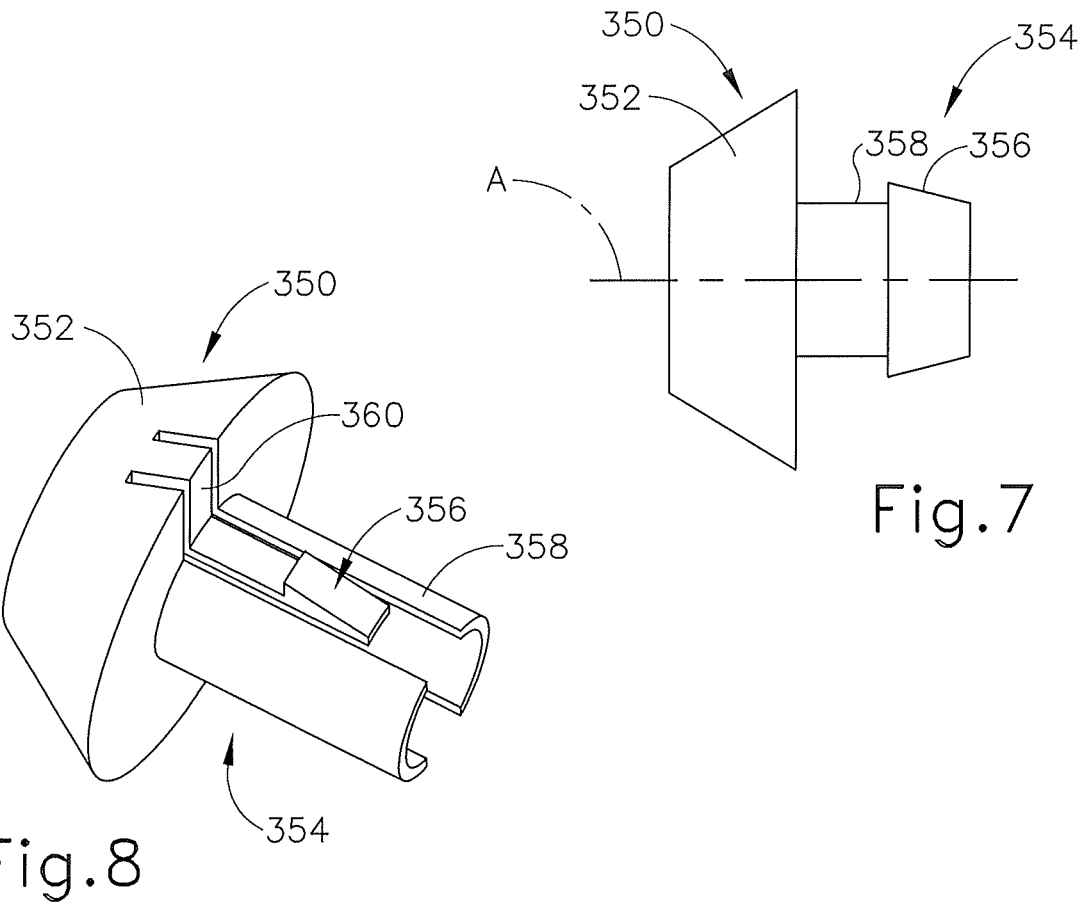
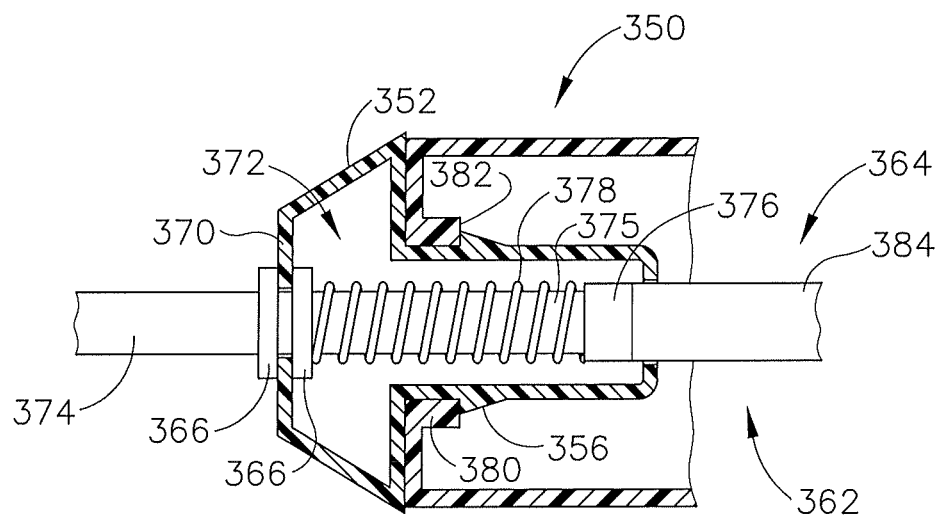
Fig.7
Fig.8
Fig.9

SURGICAL INSTRUMENT SHAFT WITH RESILIENTLY BIASED COUPLING TO HANDPIECE

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts an elevation view of an exemplary rotator including tabs;

FIG. 8 depicts a fragmentary, perspective view of the exemplary rotator of FIG. 7;

FIG. 9 depicts a cross-sectional view of the exemplary rotator of FIG. 7 coupled with an exemplary multi-piece handle assembly and a shaft;

Figure 1:
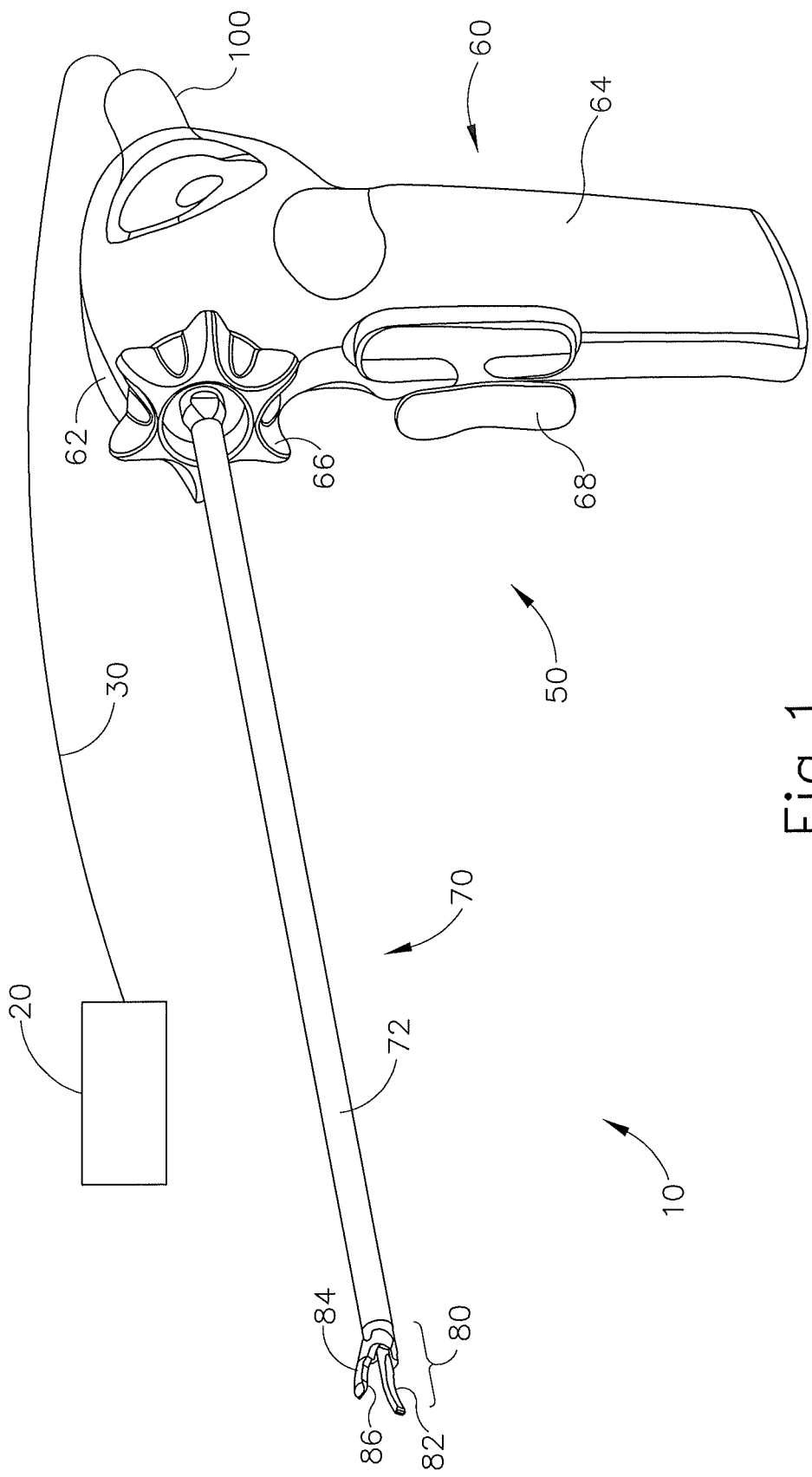
FIG. 1 depicts a perspective view of an exemplary surgical system comprising a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. Exemplary versions of end effector (80) and transmission assembly (70) will be discussed in greater detail below in reference to the example shown in FIG. 4.

In some versions, transducer (100) comprises a plurality of piezoelectric elements (not shown) that are compressed between first resonator (not shown) and second resonator (not shown) to form a stack of piezoelectric elements. The piezoelectric elements may be fabricated from any suitable material, for example, lead zirconate-titanate, lead metaniobate, lead titanate, and/or any suitable piezoelectric crystal material, for example. Transducer (100) further comprises electrodes, including at least one positive electrode and at least one negative electrode that are configured to create a voltage potential across the one or more piezoelectric elements, such that the piezoelectric elements convert the electrical power into ultrasonic vibrations. The ultrasonic vibrations are transmitted to blade (82) via the waveguide in transmission assembly (70).

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, the disclosure of which is incorporated by reference herein. Toggle buttons (69), shown in FIG. 2 of the present disclosure, are located on a distal surface of lower portion (64) and are operable to selectively activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic (such as polycarbonate or a liquid crystal polymer), ceramics, metals, and/or any other suitable material as will be apparent to one of ordinary skill in the art in view of the teachings herein. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Coupling Assemblies for Ultrasonic Surgical Instrument

In some instances it may be useful to detach transmission assembly (70) from multi-piece handle assembly (60) and transducer (100). For instance, a detachable transmission assembly (70) may permit the reuse of multi-piece handle assembly (60) with multiple transmission assemblies (70) having various end effectors (80). By way of example only, the various end effectors (80) may have different sized and/or shaped blades (82) or the various end effectors (80) may have entirely different functions, such as RF end effectors, stapling end effectors, cutting end effectors, etc. Furthermore, a single multi-piece handle assembly (60) may be reused for different operations by a user by removing a dirty transmission assembly (70), optionally cleaning multi-piece handle assembly (60), and coupling a new transmission assembly (70) to multi-piece handle assembly (60) for a new operation. Accordingly, configuring multi-piece handle assembly (60) to couple with a variety of transmission assemblies (70) may be preferable for some users of surgical instrument (50).

A. Exemplary Multi-Piece Handle Assembly

Figure 2:
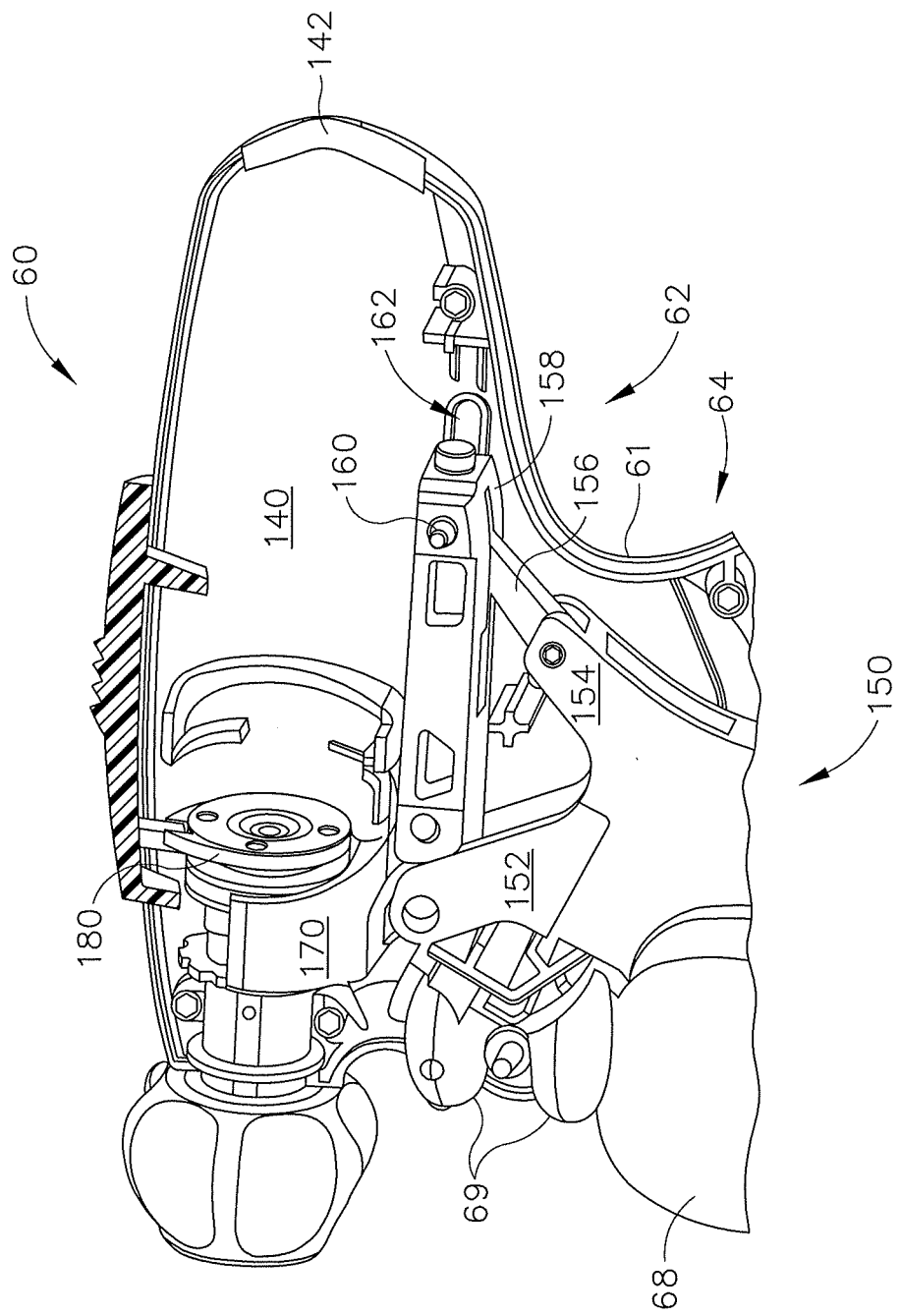
FIG. 2 depicts a partial side elevation view of an exemplary surgical instrument with a portion of a cover removed to show the interior of a mating housing portion of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (160) extending outwardly from actuation arm (158) and pins (160) are sized to be slidably received in corresponding elongated channel (162) formed in cover (61). Accordingly, when trigger (68) is pivoted proximally from the open position to the closed position attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via pins (160) within channel (162). Trigger yoke (170), which is coupled to actuation arm (158), is translated proximally as well. In the present example, trigger yoke (170) is coupled to a force-limiting mechanism (180), which is further coupled to transmission assembly (70) as will be described in more detail below, to operate inner tubular actuating member (74). A cavity (140), shown in FIG. 2, is configured to receive transducer (100) therein from a transducer aperture (142) formed in cover (61). Cavity (140) is configured to receive at least a portion of transducer (100) therein such that transducer (100) and transmission assembly (70) may be coupled together. Still other configurations for multi-piece handle assembly (60) will be apparent to one of ordinary skill in the art in view of the teachings herein.

B. Exemplary Transducer

Figure 3:
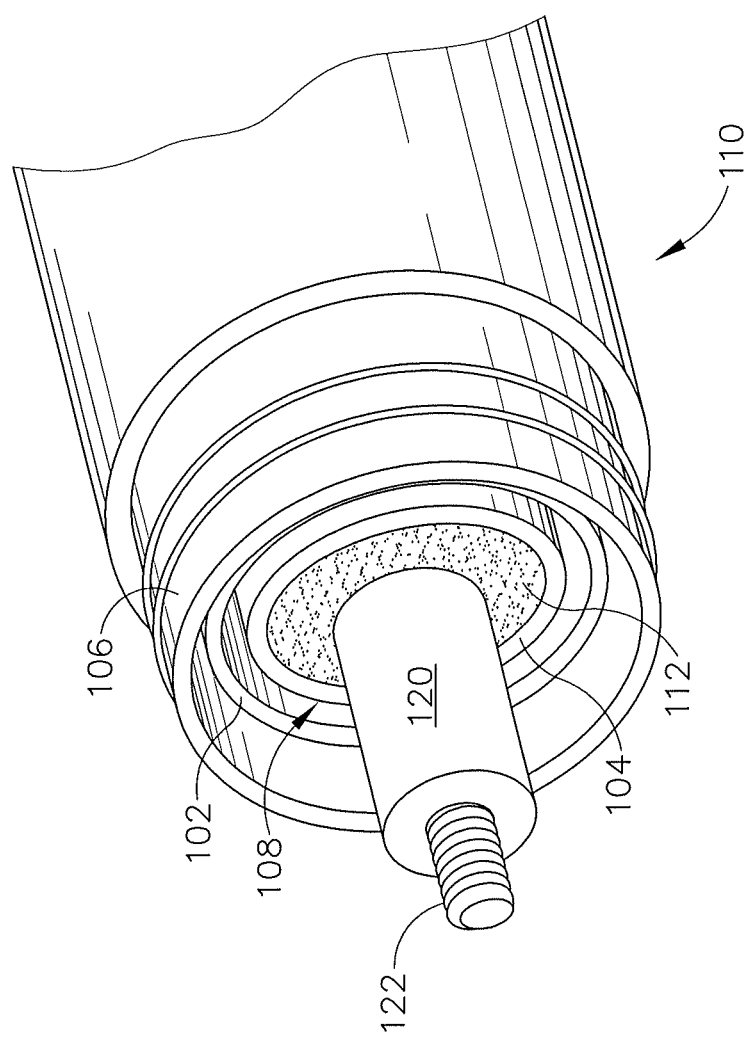
FIG. 3 depicts a partial perspective view of a distal end of an exemplary transducer.

As shown in FIG. 3, transducer (100) of the present example is a tubular component that is coupled to generator (20) via cable (30), though it should be understood that transducer (100) may instead be a cordless transducer. For instance, transducer (100) may instead receive power from a power source that is contained within handle assembly (60), in accordance with the teachings of various references cited herein or otherwise. In the present example, transducer (100) includes a first conductive ring (102) and a second conductive ring (104), which are disposed within a body (110) of transducer (100). In the present example, first conductive ring (102) comprises a ring member having one or more electrical contacts that are disposed on the ring member and that are configured to electrically couple first conductive ring (102) to a power source. First conductive ring (102) is disposed between body (110) and a horn (120) extending distally from body (110). Horn (120) comprises distal horn threads (122) such that horn (120) is coupleable to waveguide (210), as will be discussed below in reference to FIG. 4. First conductive ring (102) of the present example is coaxial with and adjacent to a flange (106). Flange (106) of the present example is configured to further mechanically couple transducer (100) within multi-piece handle assembly (60). A transducer cavity (108) is disposed between first conductive ring (102) and a second conductive ring (104) such that first conductive ring (102) is electrically isolated from second conductive ring (104) and/or other conductive components of transducer (100). First conductive ring (102) is located on a non-conductive platform extending distally from body (110). First conductive ring (102) is electrically coupled to cable (30), shown in FIG. 1, by one or more electrical wires or conductive etchings (not shown) within body (110). Such electrical coupling of first conductive ring (102) to cable (30) may include a slip ring to facilitate free rotation of transducer (100) relative to cable (30).

Second conductive ring (104) of transducer (100) similarly comprises a ring member that is disposed between body (110) and horn (120). Second conductive ring (104) is disposed between first conductive ring (102) and horn (120). As is shown in FIG. 3, first and second conductive rings (102, 104) are coaxial members. Second conductive ring (104) is likewise electrically isolated from first conductive ring (102) and other conductive components of transducer (100). Similar to first conductive ring (102), second conductive ring (104) extends from the non-conductive platform. One or more washer-shaped spacers (112) may be disposed between second conductive ring (104) and horn (120) to isolate the vibrations transmitted through horn (120) from the other components of transducer (100). Second conductive ring (104) is also electrically coupled to cable (30), shown in FIG. 1, by one or more electrical wires or conductive etchings (not shown) within body (110). Such electrical coupling of second conductive ring (104) to cable (30) may also include a slip ring to facilitate free rotation of transducer (100) relative to cable (30). One merely exemplary suitable ultrasonic transducer (100) is Model No. HP054, sold by Ethicon Endo-Surgery, Inc. of Cincinnati, Ohio, though it should be understood that any other suitable transducer may be used.

As shown in the present example, the distal end of transducer (100) threadably couples to the proximal end of a transmission assembly via horn (120). The distal end of transducer (100) also interfaces with one or more electrical connections (not shown) via first and second conductive rings (102, 104) to electrically couple transducer (100) to toggle buttons (69) to provide a user with finger-activated controls for activating transducer (100) while using surgical instrument (50). The interface between the one or more electrical connections and the first and second conductive rings (102, 104) may include a slip ring connection to permit free rotation of transducer (100) relative to multi-piece handle assembly (60). Still other configurations for transducer (100) will be apparent to one of ordinary skill in the art in view of the teachings herein. For instance, first and second conductive rings (102, 104) may be omitted from the distal end of transducer (100) and the electrical coupling of transducer (100) to toggle buttons (69) may be accomplished by alternative structures, such as conductors at the proximal end of transducer (100), conductors located along the side of body (110) of transducer (100), directly from cable (30), and/or otherwise. When transducer (100) of the present example is activated via a toggle button (69), transducer (100) is operable to create mechanical energy in the form of linear oscillations or vibrations, at an ultrasonic frequency (such as 55.5 kHz). When transducer (100) is coupled to transmission assembly (70) via horn (120), these mechanical oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one of ordinary skill in the art in view of the teachings herein.

C. Exemplary Transmission Assembly for Threaded Attachment

As noted previously, in some instances it may be useful to detach transmission assembly (70) from multi-piece handle assembly (60) and transducer (100). Merely exemplary instances include the use of multi-piece handle assembly (60) with multiple transmission assemblies (70) having different sized and/or shaped blades (82), use with various end effectors (80) with entirely different functions and/or modalities (e.g., RF end effectors, stapling end effectors, cutting end effectors, etc.), or for reuse of a single multi-piece handle assembly (60) for multiple operations by a user. Accordingly, a version permitting the user to swap transmission assemblies (70) with multi-piece handle assembly (60) may be useful.

Figure 4:
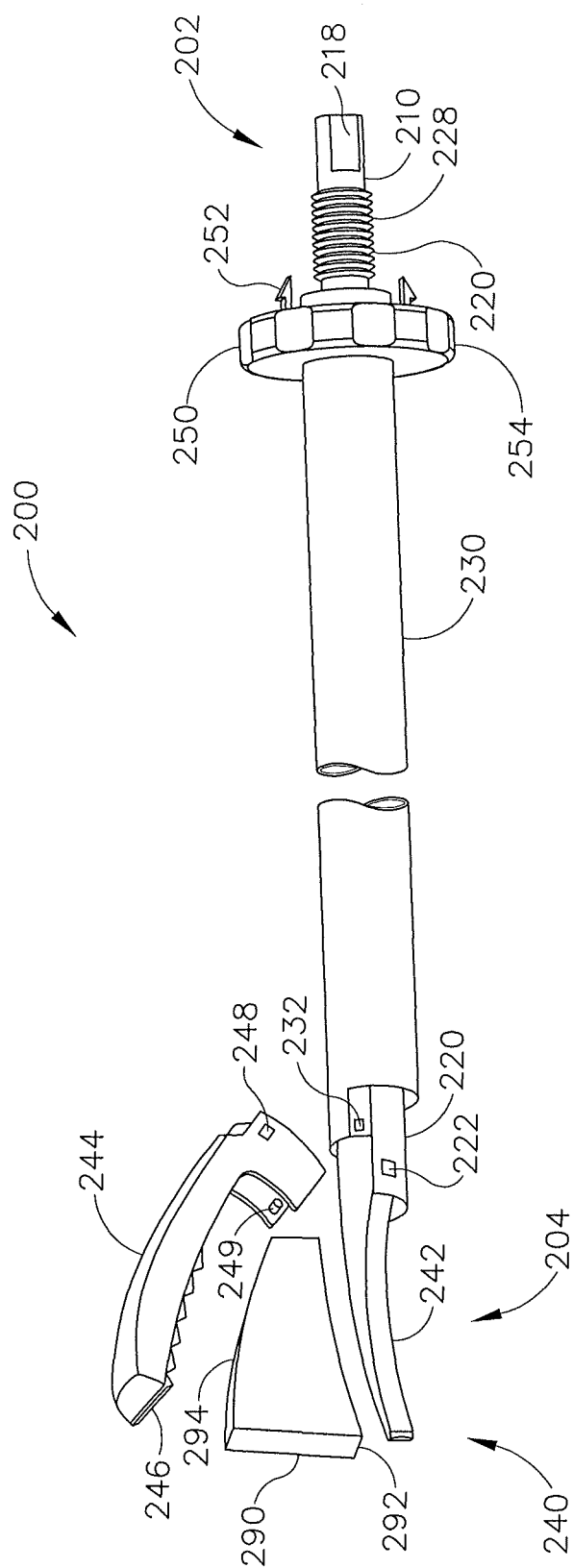
FIG. 4 depicts a perspective view of an exemplary transmission assembly.

One merely exemplary transmission assembly (200) is shown in FIG. 4 having a proximal end (202), a distal end (204), a waveguide (210), an inner tubular actuating member (220), an outer sheath (230), and an end effector (240) at the distal end of transmission assembly (200). In the present example, waveguide (210), inner tubular actuating member (220), and outer sheath (230) are coaxial members with waveguide (230) in the center, inner actuating member (220) disposed about waveguide (210), and outer sheath (230) disposed about inner actuating member (220).

Referring to distal end (204) of transmission assembly (200) first, end effector (240) comprises a blade (242), a clamp arm (244), and one or more optional clamp pads (246). In the present example, blade (242) is coupled to waveguide (210) such that the mechanical vibrations transmitted to waveguide (210) from transducer (100) are also transmitted to blade (242). Merely exemplary couplings for blade (242) to waveguide (210) include welding blade (242) to waveguide (210), integrally forming blade (242) with waveguide (210), mechanically or chemically coupling blade (242) to waveguide (210), and/or any other suitable configuration as will be apparent to one of ordinary skill in the art in view of the teachings herein. In some versions, blade (242) is a curved blade, such as blade (242) shown in FIG. 4; and in some versions blade (242) may be a straight blade. Furthermore, blade (242) may have a variety of shapes and sizes. In the present example, blade (242) is a tapered rectangular blade, though it should be understood that blade (242) may be cylindrical, triangular, hemi-cylindrical, square, hooked, and/or any other shape for blade (242). Furthermore, additional features may be added to blade (242), including spherical tips, hooked tips, square tips, serrated edging, and/or any other additional features. Still other configurations for blade (242) will be apparent to those of ordinary skill in the art in view of the teachings herein.

Clamp arm (244) of the present example is a curved member that corresponds to the curvature of blade (242). Clamp arm (244) may optionally include clamp pads (246) to grip or secure tissue against blade (242). Such clamp pads may be configured in accordance with at least some of the teachings of U.S. Pat. Pub. No. 2006/0079874, entitled "Tissue Pad Use with an Ultrasonic Surgical Instrument," published Apr. 13, 2006. Pivotal movement of clamp arm (244) with respect to blade (242) is accomplished by a first pair of pivot points (248) on clamp arm (244) that pivotally couple to outer sheath (230) and a second set of pivot points (249) on clamp arm (244) that pivotally couple to inner tubular actuating member (220). In the present example, outer sheath (230) is coupleable to multi-piece handle assembly (60) through a rotation knob (250), thereby grounding outer sheath (230). First set of pivot points (248)

of clamp arm (244) are pivotally connected to outer sheath (230) via corresponding through holes (232) on outer sheath (230). In some versions, first set of pivot points (248) comprise through holes and a securing pin or rivet may be inserted through first set of pivot points (248) and through through holes (232) to secure clamp arm (244) to outer sheath (230). The pin in this version may be laser welded to clamp arm (244) or the pin may be laser welded to outer sheath (230). Of course through holes (232) may instead be outwardly extending pins and first set of pivot points (248) may be through holes. Still other configurations for first set of pivot points (248) and through holes (232) will be apparent to one of ordinary skill in the art in view of the teachings herein.

Second set of pivot points (249) of clamp arm (244) are pivotally connected to inner tubular actuating member (220) via corresponding through holes (222) on inner tubular actuating member (220). In some versions, second set of pivot points (249) comprise through holes and a securing pin or rivet may be inserted through second set of pivot points (249) and through through holes (222) to secure clamp arm (244) to inner tubular actuating member (220). The pin in this version may be laser welded to clamp arm (244) or the pin may be laser welded to inner tubular actuating member (220). Of course through holes (222) may instead be outwardly extending pins and second set of pivot points (249) may be through holes. Still other pivotable configurations for second set of pivot points (249) and through holes (222) will be apparent to one of ordinary skill in the art in view of the teachings herein.

With clamp arm (244) so secured to outer sheath (230) and inner tubular actuating member (220), clamp arm (244) is pivotable when inner tubular actuating member (220) translates longitudinally. In the present example, inner tubular actuating member (220) is translatable relative to the longitudinal axis of outer sheath (230) and is coupled to force-limiting mechanism (180) within multi-piece handle assembly (60). Thus, when force-limiting mechanism (180) translates via trigger (68) and trigger assembly (150), clamp arm (244) is pivotable from an open position to a closed position. It should be understood that, as with other components referred to herein, clamp arm (84, 244) is merely optional. Likewise, trigger (68) and trigger assembly (150) and the components described herein for pivoting clamp arm (84, 244) are also merely optional. Thus, some versions of end effector (80, 240) may simply consist of a blade (82, 842) and/or other features.

As shown in FIG. 4, a spacer (290) is insertable between clamp arm (244) and blade (242) to maintain clamp arm (244) in the open position. Spacer (290) has a flat bottom surface (292) and an angled top surface (294) in this example. Top surface (294) is set at an angle to maintain clamp arm (244) in the open position relative to blade (242) when bottom surface (292) abuts blade (242). In some versions, bottom surface (292) may be configured to snap or clip onto blade (242) to secure spacer (290) relative to blade (242). Alternatively, a recess may be provided in spacer (290) such that spacer (290) may be slid onto blade (242). Further still, an adhesive may be applied to bottom surface (292) and/or top surface (294) to also secure spacer (290). Thus, when spacer (290) is inserted between clamp arm (244) and blade (242), clamp arm (244) is prevented from pivoting to a closed position. This may permit a user to couple transmission assembly (200) to multi-piece handle assembly (60) while maintaining both clamp arm (244) and trigger (68) in their respective open positions. Alternatively, a user may couple transmission assembly (200) to multi-piece handle assembly (60) without the use of spacer (290). For example, the user may couple different components of transmission assembly (200) with different components of handle assembly (60) at different times, such as in the manner described below or otherwise.

Referring now to distal end (202) of transmission assembly (200), a rotation knob (250) couples outer sheath (230) to multi-piece handle assembly (60). In the present example, rotation knob (250) comprises an inner ring portion (not shown) having one or more connectors (252) extending proximally therefrom, an outer ring (254), and a pin (not shown) extending through outer ring (254), outer sheath (230), inner tubular actuating member (220), and waveguide (210). Accordingly, when outer ring (254) of rotation knob (250) is rotated, waveguide (210), inner tubular actuating member (220), and outer sheath (230) also rotate. Inner ring portion and outer ring (254) of the present example are complementary bearing components such that outer ring (254) is rotatable relative to inner ring portion. It should be understood that the pin does not extend though inner ring portion. As previously noted, inner ring portion includes connectors (252). In the present example connectors (252) are shown as snap-fit connectors, though other suitable connecting features, such as threading, adhesives, pins, clips, snaps, and/or other connectors may be used as will be apparent to one of ordinary skill in the art in view of the teachings herein. When transmission assembly (200) is assembled with multi-piece handle assembly (60) and transducer (100), as will be discussed below, connectors (252) of the present example insert into one or more recesses (not shown) and couple rotation knob (250) to cover (61) of multi-piece handle assembly (60). A release mechanism, such as a push button (not shown) on multi-piece handle assembly (60) or on rotation knob (250) may be provided to decouple connectors (252) from cover (61) when transmission assembly (200) is to be removed. Alternatively, connectors (252) may be designed to break-away when transmission assembly (200) is decoupled. Further still, if threading is used, inner portion of rotation knob (250) may be rotated to decouple from multi-piece handle assembly (60). Still other suitable configurations for rotation knob (250) will be apparent to one of ordinary skill in the art in view of the teachings herein.

Still referring to proximal end (202) of transmission assembly (200), external threads (228) are included at the proximal end of inner tubular actuating member (220) as shown in FIG. 4. External threads (228) screw into complementary threads (not shown) of force-limiting mechanism (180), which is in turn driven by trigger assembly (150). Additionally, a recess having internal threading (218) is included at the proximal end of waveguide (210) as shown in FIG. 4. Internal threading (218) screws onto horn threads (122) to mechanically and acoustically couple waveguide (210) to transducer (100). Of course other suitable configurations for transmission assembly (200) will be apparent to one or ordinary skill in the art in view of the teachings herein. Similarly, various other suitable ways in which transmission assembly (200) may be coupled with handle assembly (60) will be apparent to those of ordinary skill in the art in view of the teachings herein.

III. Exemplary Removable Shaft Connections to Handle Portions

Versions described below discuss connections and uses of disposable transmission assemblies that are alternative versions of transmission assembly (70) described above. The alternative versions of transmission assembly (70) include components that permit the alternative transmission assemblies to be selectively coupleable and adjustable with transducer (100), for example, in respective reusable handle portions of ultrasonic surgical instruments. Additional exemplary modifications that may be provided for transmission assembly (70) selectively coupleable to multi-piece handle assembly (60) and transducer (100) of instrument (50) will be described in greater detail below. Various suitable ways in which the below teachings may be incorporated into instrument (50) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (50) or devices taught in the references cited herein. The below teachings may be readily applied to various other kinds of instruments, including instruments that would not be classified as ultrasonic surgical instruments. Various other suitable devices and settings in which the below teachings may be applied will be apparent to those of ordinary skill in the art in view of the teachings herein.

A. Exemplary Ball Detent Connection

Figure 5:
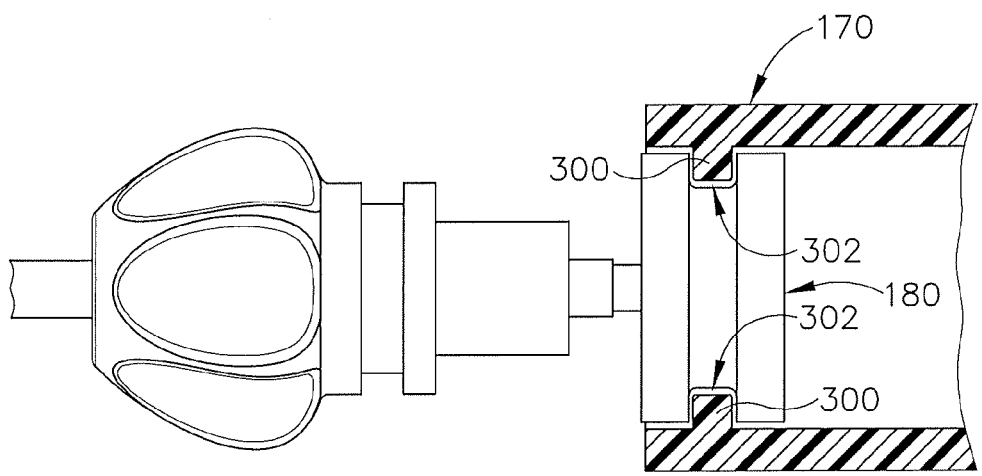
FIG. 5 depicts a partial view of the proximal end of an exemplary transmission assembly coupled to the distal end of an exemplary handle assembly.

FIG. 5 shows the connection of yoke (170) to force-limiting mechanism (180) of transmission assembly (70). Yoke (170) includes posts (300) which are captured within notches (302) in force-limiting mechanism (180). Posts (300) transmit force such as a high, distally oriented closure force to drive a clamping portion of the end effector for good vessel coaptation during cutting; and a smaller, proximally oriented opening force for dissection.

Figure 6:
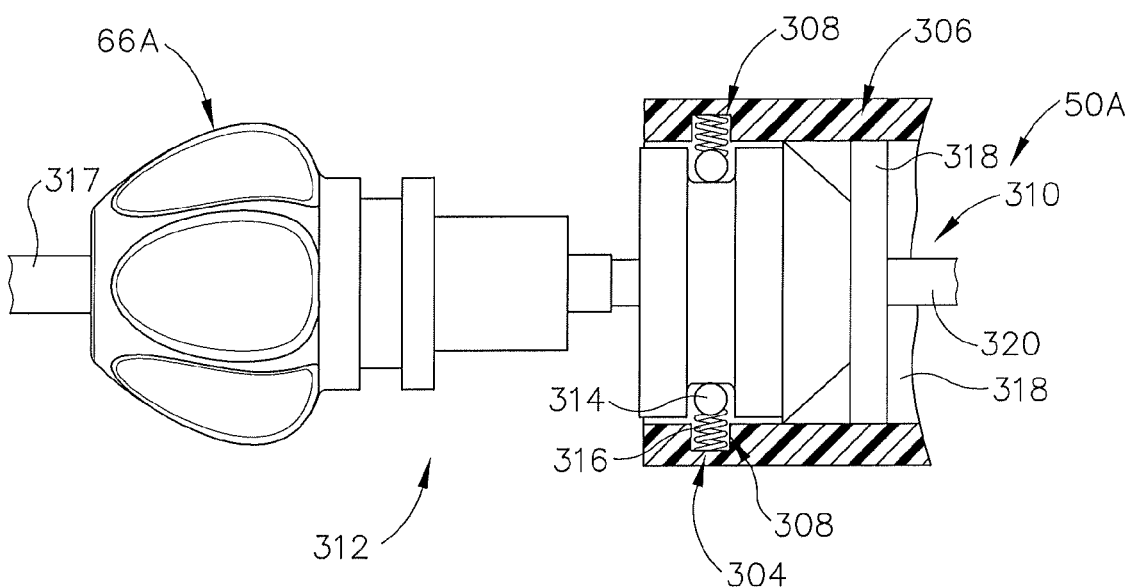
FIG. 6 depicts a partial view of the proximal end of another exemplary transmission assembly coupled to the distal end of another exemplary handle assembly.

FIG. 6 shows an alternative version using spring loaded ball detents assembly (304) in yoke (306) rather than posts to latch into notches (308) defined within proximal end (310) of transmission assembly (312). Spring loaded ball detents assembly (304) includes ball bearings or detents (314) attached to ends of biasing members such as springs (316). Detents (314) assist to connect transmission assembly (312) to mating housing portion (62A) of cover (61A) of surgical instrument (50A). Surgical instrument (50A) is similar to surgical instrument (50) described above with the exception of the differences described below regarding the connection and release of the transmission assembly (312) respectively to and from surgical instrument (50A). The same applies to other versions of surgical instruments described below and herein. Similarly, versions of transmission assemblies described below and herein each include a rotation knob, such as knob (66A), and a shaft, such as outer sheath (317), which is similar to outer sheath (72) of transmission assembly (70) and outer sheath (230) of transmission assembly (200). Outer sheath (317) may rotate relative to the handpiece of instrument (50A) but does not translate relative to the handpiece.

When connecting transmission assembly (312) to a reusable handle portion of surgical instrument (50A), proximal end (310) of assembly (312) pushes detents (314) outwardly and away from assembly (312) until detents (314) are aligned with notches (308), at which point springs (316) apply a biasing force to mate detents (314) with notches (308). This force removably connects assembly (312) to yoke (306) of instrument (50A). Yoke (306) is similar to yoke (170) of transmission assembly (70). Yoke (306) translates within the handpiece of instrument (50A) based on pivotal movement of the trigger (not shown) relative to the handpiece, where the trigger is similar in structure and operation to trigger (68) of transmission assembly (70). Proximal end (310) of assembly (312) includes an inner tube portion similar to inner tubular actuating member (220) of transmission assembly (200). The inner tube portion of proximal end (310) translates within yoke (306) relative to the handpiece of instrument (50A) and includes an internal tube extending through and translating within outer sheath (317). When the internal tube translates in a first direction (e.g., proximally), the internal tube pivots clamp arm (244) toward blade (242). When the internal tube translates in a second, opposite direction (e.g., distally), the internal tube pivots clamp arm (244) away from blade (242).

In some other versions, the internal tube may remain stationary while outer sheath (317) translates distally to close clamp arm (244) against blade (242). As another merely illustrative variation, the internal tube may engage pivots on clamp arm (244) and outer sheath (317) may engage fixed driver pins, thus allowing for a distal motion of internal tube to close clamp arm (244) against blade (242). Yet another merely illustrative version involves having both pivot pins and drive pins positioned on an upper side of clamp arm (244), with the drive pins disposed slightly higher than the pivot pins, such that distal translation of the internal tube would close clamp arm (244) against blade (242). In yet another version, standoff yoke surface (318), described in greater detail below, may be disposed at a distal end of yoke (306) and include a lip that a proximal end of assembly (312) snaps over during insertion. Such insertion and structure would allow for a strong, proximal pull working against a weaker, distal push when assembly (312) is so attached to yoke (306). Other suitable ways in which clamp arm (244) may be actuated will be apparent to those of ordinary skill in the art in view of the teachings herein.

A waveguide (320) is similar to waveguide (210) of transmission assembly (200) and is coaxially positioned within outer sheath (317) and within the internal tube. Waveguide (320) extends proximally relative to proximal end (310) of assembly (312) and couples with a transducer (not shown).

As the assembly (312) may be rotated, the waveguide could still be screwed into the transducer, as described above with respect to FIGS. 3 and 4, after the connection to yoke (306) is made. Once in position, proximal end (310) of assembly (312) sits flush against a standoff yoke surface (318). Standoff yoke surface (318) includes an opening for receipt of waveguide (320) of assembly (312). Standoff yoke surface (318) acts as a "setoff" for pushing on proximal end (310) of assembly (312) and allowing for a strong distal pushing force against assembly (312) and a concurrent less strong proximal pulling force. Closure of the clamp arm of the end effector of assembly (512) is then accomplished by pulling the inner tube of assembly (512) via yoke (306), against which proximal end (310) of assembly (312) sits flush via standoff yoke surface (318), allowing sufficient force to open the end effector and unclamp the end effector from tissue as described above.

When the end effector is opened, detents (314) pull on proximal end (310) of assembly (312) without disengaging from assembly (312). However, if a user wishes to replace assembly (312), the user may decouple detents (314) from assembly (312) by pulling hard enough to provide a sufficient force to remove assembly (312) from the reusable handle portion of instrument (50A).

B. Exemplary Rotator Connections

FIGS. 7-12 show three versions of exemplary rotator connections to ultrasonic surgical instruments to provide for attachment and detachment of transmission assemblies to handle portions of the surgical instruments. The first version, shown in FIGS. 7-9, is directed to detents on a cylindrical portion of a rotator and a shaft connection method including a spring return. The second version, shown in FIG. 10, utilizes a shaft connection method including a retention ring. The third version, shown in FIGS. 11 and 12, utilizes a shaft connection method including a resiliently biasing clamping component in the form of multiple retention arms.

1. Exemplary Detent and Spring Return Version

FIG. 7 shows rotator (350) including knob portion (352) and proximal portion (354) transversely projecting from knob portion (352). Proximal portion (354) includes tabs (356) projecting from cylindrical portion (358). Rotator (350) includes longitudinal axis (A), which in FIG. 7 divides rotator (350) into two portions. FIG. 8 shows a fragmentary, perspective view of one of those portions. Tab (356) projects from the free end of resilient arm (360).

FIG. 9 shows a cross sectional view of rotator (350) as part of transmission assembly (362) inserted into distal end (364) of an ultrasonic surgical instrument. Assembly (362) includes a pair of stops (366) that capture a distal wall (370) of rotator (350). Distal wall (370) and other external walls of rotator (350) define an interior hollow space (372) through which inner tube (375) runs. Inner tube (375) translates within outer sheath (374). End piece (376) is fixedly disposed on a proximal end of inner tube (375) at a location aligned with a proximal end of cylindrical portion (358) when assembly (362) is fully inserted in distal end (364) of the instrument. A biasing member such as spring (378) is disposed between one of stops (366) and end piece (376). End piece (376) biases inner tube (375) to a proximal position, thereby biasing clamp arm (244) to a closed position (pivoted toward blade (242)).

Additionally, when assembly (362) first inserted in distal end (364) of the instrument, tabs (356) compress inwards when against an aperture formed in distal end (364) which receives assembly (364). Cylindrical walls (380) defining the aperture end in ledges (382). When assembly (362) is fully inserted in distal end (364) of the instrument, tabs (356) clear cylindrical walls (380) and spring outward such than an upper surface of each tab (356) sits flush against ledges (382) to prevent undesired removal of assembly (362) from distal end (364). Rotator (350) may be removed thereafter by depressing tabs (356) by, for example, a user's fingers, to allow detents or tabs (356) to clear back through the aperture defined by walls (380).

A drive member (384) engages end piece (376) when assembly (362) is fully seated in the handpiece. Drive member (384) may be actuated via a yoke feature, in a manner as described above for surgical instrument (50), to compress spring (378) and push inner tube (375) distally in a manner closing a connected end effector (also as described above for instrument (50)). Releasing the trigger releases spring (378) from a compressed state such that the biasing force of spring (378) drives inner tube (375) proximally and re-opens the clamped end effector (as described above). While the above described inner tube (375) is described as a clamp arm actuating tube for an ultrasonic surgical instrument (50), a similar inner member could be used as a firing beam for a radio frequency based surgical instrument or surgical stapling instrument (e.g., endocutter, etc.), including but not limited to variations of such instruments described in various references cited herein.

2. Exemplary Ring Version

Figure 10:
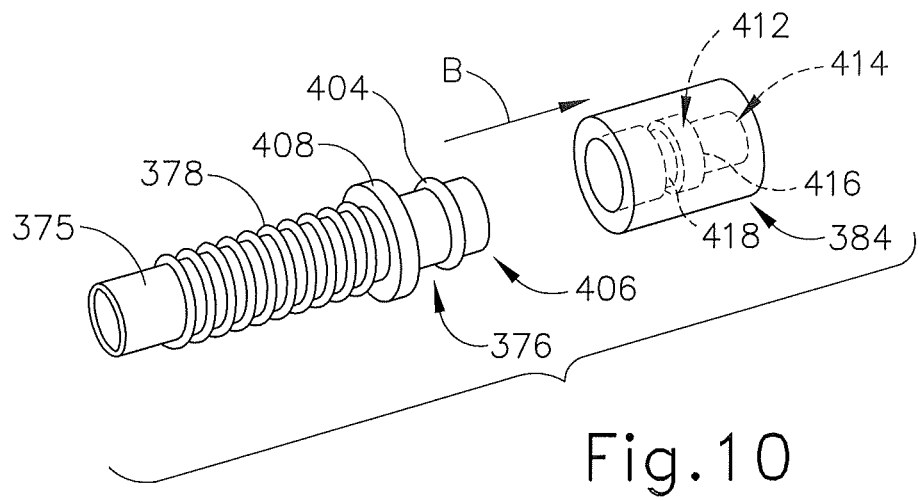
FIG. 10 depicts a perspective view of an alternative version of a connection of an exemplary shaft to a drive member.

FIG. 10 shows a manner of connecting end piece (376) of FIG. 9 to drive member (384) of FIG. 9. Retention ring (404) is disposed in a groove at a proximal portion of end piece (376) between proximal end (406) and stop (408). Ring (404) helps to retain end piece (376) within drive member (384) while still allowing spring (378) disposed about inner tube (375) to return end piece (376) in the direction of arrow (B) to an initial, home position when a trigger on the instrument is not released. Ring (404) has a radial spring characteristic, allowing ring (404) to compress when end piece (376) is inserted into drive member (384). For instance, ring (404) may include a gap allowing the effective diameter of ring (404) to reduce as ring (404) is driven into first internal bore portion (412) of drive member (384), described below.

End piece (376) is inserted into drive member (384) in the direction of arrow (B). Drive member (384) includes first internal bore portion (412) disposed distal to second internal bore portion (414), which is narrower than portion (412) and separated from portion (412) via ledge (416), against which proximal end (406) will abut. First internal bore portion (412) of drive member (384) also includes annular groove (418) configured to receive ring (404). Ring (404) will have sufficient retention force to transmit force from spring (378) to return end piece (376) to the initial, home position, but such retention force may be overcome to remove end piece (376) from drive member (384) by pulling distally on transmission assembly (362). Alternatively, ring (404) may be positioned on a portion of the handle of the instrument rather than on end piece (376) to act as retention means against a groove in end piece (376).

3. Exemplary Retention Arms Version

Figure 11:
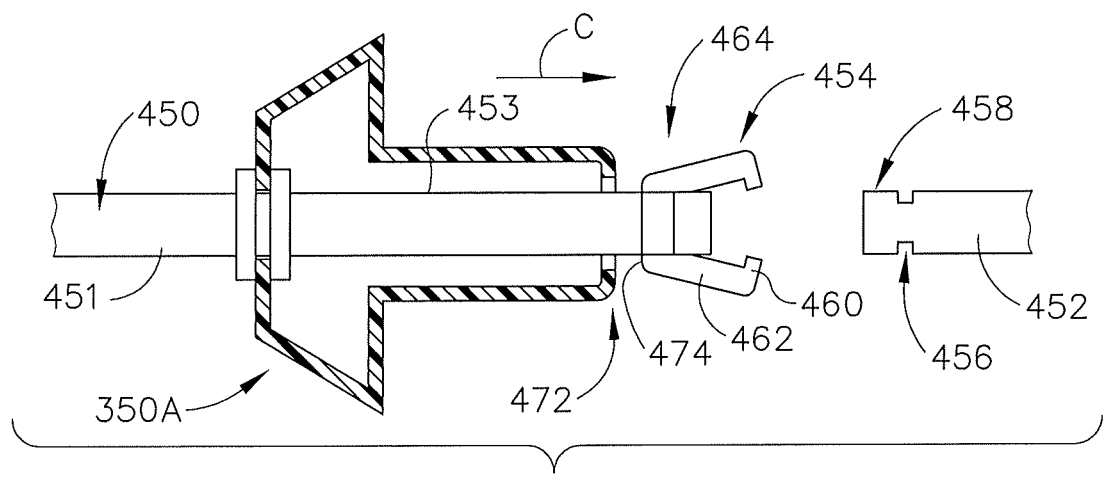
FIG. 11 depicts a cross-sectional view of an alternative version of a connection of an exemplary shaft to a drive member in an unlocked position.
Figure 12:
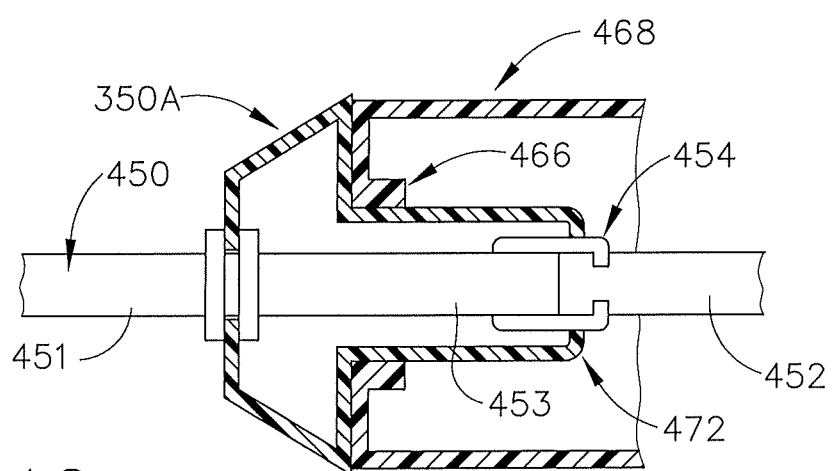
FIG. 12 depicts the exemplary shaft and drive member of FIG. 11 in a locked position.

FIGS. 11-12 show another manner of connecting another version of a shaft assembly (450), including outer sheath (451) with an internally translating inner tube (453), to drive member (452) via a resiliently biased clamping component (454). For example, FIG. 12 shows a manner of connecting a version of inner tubular actuating member (220) to yoke (170) and force-limiting mechanism (180) of transmission assembly (70), where inner tube (453) is similar to inner tubular actuating member (220). Shaft assembly (450) may still be used with rotator (350) described above to retain the transmission assembly to the instrument.

Drive member (452) shown in FIG. 11 includes groove (456) formed in distal end (458) of drive member (452). Groove (456) is configured to receive wedges (460) inwardly extending from retention arms (462) of component (454). Retention arms (462) are naturally or resiliently biased outward. Component (454) is disposed at proximal end (464) of inner tube (453) of shaft assembly (450). Component (454) may be molded in the described shape or could be a stamped metal, such as spring steel or other such suitable material.

When component (454) of inner tube (453) is inserted into circular recess (466) within distal end (468) of the handpiece (not shown) of the instrument in the direction of arrow (C), as shown in FIG. 11, shaft assembly (450) progresses until proximal end (470) abuts a surface on distal end (458) of drive member (452). At this point, proximal end (472) of rotator (350A), which includes a proximal recess portion, will receive and clamp about distal end (474) of component (454). The internal walls defining the proximal recess portion of proximal end (472) of rotator (350A) will continue to advance over retention arms (462) to compress arms (462) inwards until wedges (460) are received in groove (456), as shown in FIG. 12. Once rotator (350A) is fully inserted into distal end (468) of the instrument, arms (462) cannot open outward to the natural position until rotator (350A) is moved distally out of distal end (468) of the instrument, at which point arms (462) bias outward to their natural position to release drive member (452) from shaft assembly (450). One or more additional components may be provided to selectively secure rotator (350A) to distal end (468) of the instrument. Various suitable forms that such components may take will be apparent to one of ordinary skill in the art in view of the teachings herein.

C. Exemplary Ball Bearing Compression Lock Connection

Figure 13:
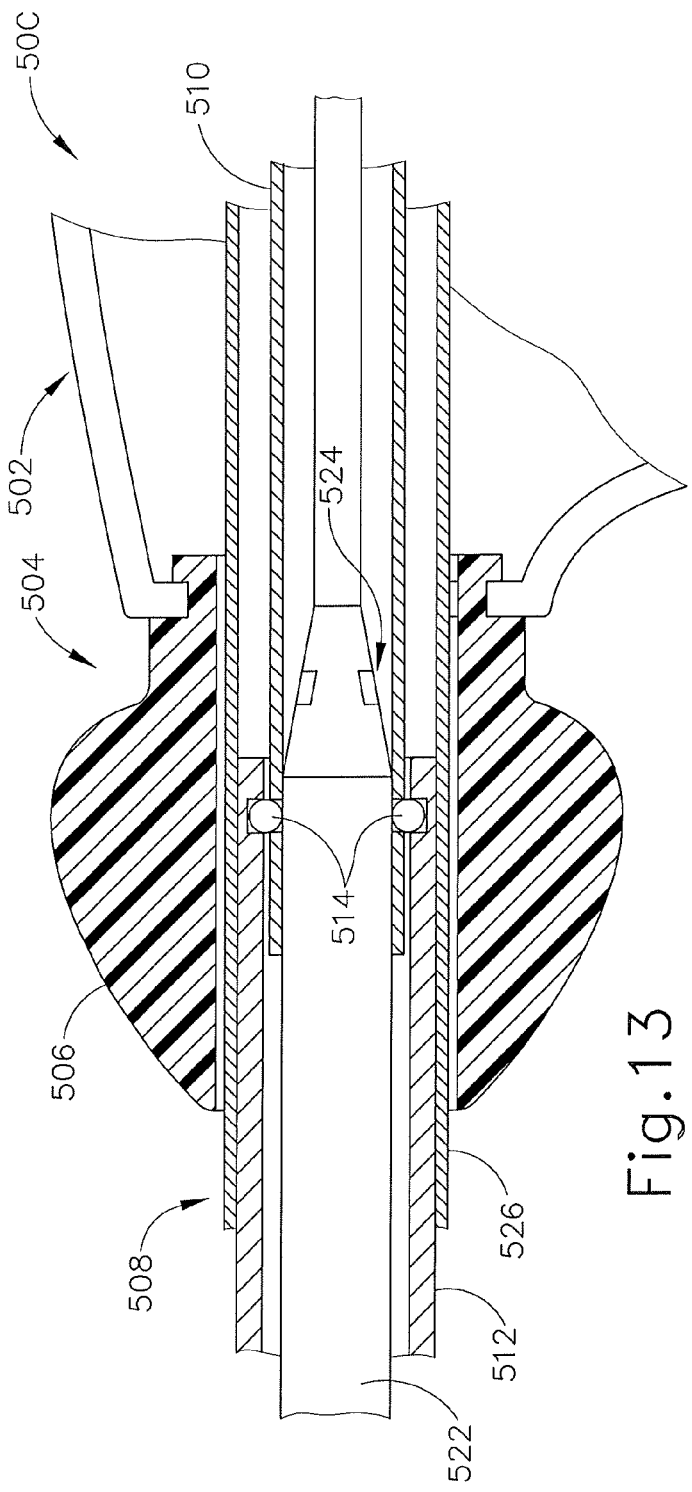
FIG. 13 depicts a partial view of the proximal end of a transmission assembly coupled with the distal end of a handle assembly.
Figure 14:
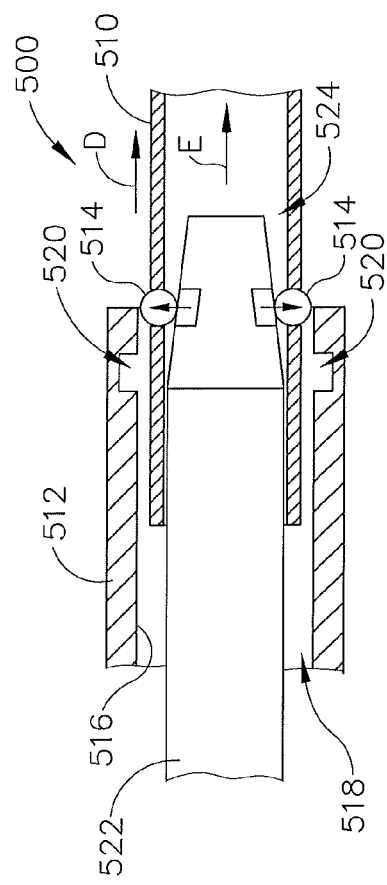
FIG. 14 depicts a partial view of the transmission assembly of FIG. 13 decoupling from the handle assembly of FIG. 13.

FIGS. 13-14 shows the connection of another transmission assembly (500) to handle portion (502) at distal end (504) of surgical instrument (50C). Assembly (500) includes a rotation knob (506) into which shaft portion (508) comprising tubes that are part of a transmission assembly, such as transmission assembly (70) described above, connect. A difference is the ball bearing manner of connection of shaft portion (508) to knob (506). In particular, as shown in FIG. 13, drive member (510) is connected to inner tube (512) via ball bearings (514). FIG. 14 shows inner tube (512) proximally progressing in the direction of arrow (D). Inner tube (512) includes inner circular walls (516) defining inner recess (518). An annular notch (520) is further defined in walls (516). Notch (520) is configured to receive ball bearings (514).

During assembly, waveguide (522) progresses in the direction of arrow (E) within both inner tube (512) and a recess within drive member (510). Waveguide (522) includes a tapered proximal end (524) such that when tapered end (524) progresses in the direction of arrow (E), ball bearings (514) engage with the tapered end (524) to ride up the widening ramped surface and are forced into engagement with notch (520) via a camming force applied by waveguide (522). The strong engagement allows for a high load fitting with reduced to no longitudinal slop. Further, inner tube (512) may still be rotated with respect to drive member (510).

Outer tube (526) and inner tube (512) connect to knob (506) via bayonet locks comprising a pin and slot type of fastening. For example, outer tube (526) ground locks into a recess ring boss (not shown) in rotation knob (506) to be fixed with respect to knob (506), which acts as a mechanical ground component. After the connection, the shaft components of transmission assembly (500) may rotate together and may still be removable from handle portion (502). Additionally, knob (506) of the present example is removably connected to handle portion (502). Inner tube (512) is similar to inner tubular actuating member (220) of transmission assembly (200). Inner tube (512) thus acts to drive a clamp arm to pivot relative to a blade, just like member (220) drives clamp arm (244) to pivot relative to blade (242) as described above.

D. Exemplary Tapered Waveguide Connection

Figure 15:
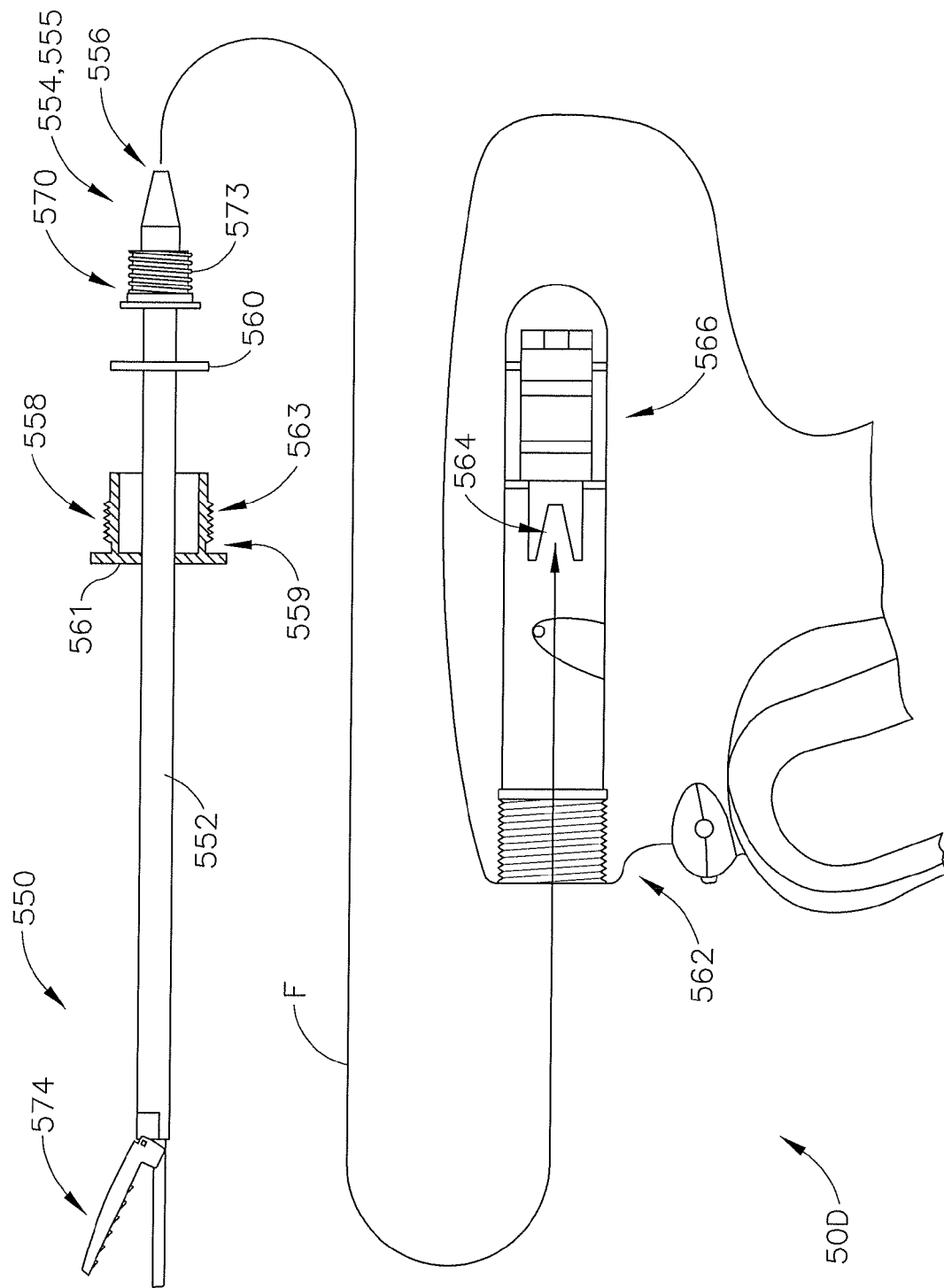
FIG. 15 depicts an elevation view of an exemplary surgical instrument having a tapered male waveguide end configured to non-threadably attach to a corresponding tapered female transducer end.

In some versions, a waveguide may be attached to a transducer in a non-threaded connection to mate a transmission assembly with a reusable handle. For example, FIG. 15 shows such a connection in an exemplary ultrasonic surgical instrument (50D). Shaft assembly (550) includes shaft (552). Waveguide (554) extends from proximal end (556) of shaft (552). Waveguide (554) includes a male end feature (555). In the present example, male end feature (555) is tapered, though it should be understood that male end feature (555) may have various other suitable shapes and forms as will be apparent to one of ordinary skill in the art in view of the teachings herein, such as a flat form or a ball form, etc. Slip nut (558) is disposed around shaft (552). Slip nut (558) is configured to contact pin (560), which is attached at a longitudinal vibratory node of waveguide (554). Threaded cap or slip nut (558) presses against nodal pin (560) at the node and generates a compressive load to couple waveguide (554) to transducer (566) without utilizing a threaded connection between waveguide (554) and transducer (566), as described below. Additionally, slip nut (558) can act as a seal. A possible seal location is at notch (559) formed between distal end (561) and threads (563) of slip nut (558).

Slip nut (558) is also configured to be threaded into handle assembly (562) of instrument (50D). The threaded connection forces end feature (555) of waveguide (554) into cavity (564), which is tapered in the present example and defined within the horn of transducer (566), along the direction of arrow (F). Cavity (564) may have various other suitable shapes and forms as will be apparent to one of ordinary skill in the art in view of the teachings herein, such as a flat form or a cone form for receipt of, for example, end feature (555) in a flat form or ball form, respectively. In particular, cavity (564) is configured to receive a correspondingly formed end feature (555). Spring mechanisms (not shown) in slip nut (558) or in transducer (566) may act to prevent too much force over the desired amount from being delivered to the connection of waveguide (554) and transducer (566). For example, in some versions, pin (560) may fit inside an inner diameter of slip nut (558), which would internally include a compression spring (not shown). A distal end of the compression spring would rest against a proximal part of a recess within slip nut (558). A drive plate (not shown) would be disposed at a proximal end of the compression spring. The drive plate would be configured to fit within the recess of slip nut (558). The drive plate would contact pin (560) and, via the compression spring, would limit force applied to pin (560). Other suitable force limiting features and configurations will be apparent to those of ordinary skill in the art in view of the teachings herein.

Spring stack washer (570) is similar to force-limiting mechanism (180) of transmission assembly (70). Handle assembly (568) interfaces with spring stack washer (570) for actuation when trigger (572) is pressed, resulting in spring (573) to be compressed. This compression causes an inner tube of shaft (552) to be driven forward to close end effector (574) in a manner similar to that described above for instrument (50). In use, shaft assembly (550) is disposable and quickly able to be attached to a reusable handle of instrument (50D).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a handle assembly comprising:
      i. a trigger,
      ii. a housing having a distal aperture formed in a distal end of the housing, and
      iv. a drive member in communication with the trigger such that actuation of the trigger is configured to actuate the drive member in a first direction; and
   (b) a transmission assembly comprising:
      i. a proximal shaft portion received within the distal aperture,
      ii. a rotator knob, the rotator knob having a proximal portion and a distal portion, the proximal portion received within the distal aperture, and the distal portion projecting distally from distal end of the housing, the proximal portion having a coupling feature configured to removably couple the rotator knob relative to the housing, wherein the coupling feature is further configured to uncouple the rotator knob relative to the housing such that the proximal portion of the rotator knob is configured to be removed distally from the distal aperture of the housing,
      iii. a distal shaft assembly extending distally relative to the rotator knob, and
      iv. an end effector coupled to a distal end of the distal shaft assembly;

wherein the drive member of the handle assembly is removably coupled to the proximal shaft portion of the transmission assembly, and wherein the proximal shaft portion of the transmission assembly is configured to be removed distally from the distal aperture of the housing.

2. The surgical instrument of claim 1, wherein the coupling feature on the proximal portion of the rotator knob includes tabs configured to abut ledges defining a portion of the distal aperture of the housing when the transmission assembly is removably coupled to the handle assembly.

3. The surgical instrument of claim 2, wherein the tabs are resiliently biased to abut the ledges.

4. The surgical instrument of claim 1, wherein the proximal shaft includes a spring disposed on the proximal shaft portion.

5. The surgical instrument of claim 4, wherein when the drive member is removably coupled to the proximal shaft portion, wherein the trigger is operable to move the drive member distally from a first position to a second position to compress the spring in the second position.

6. The surgical instrument of claim 5, wherein the trigger is further operable to release the spring, releasing a biasing force to move the drive member proximally back to the first position.

7. The surgical instrument of claim 1, further comprising a spring disposed on the proximal shaft portion and a retention ring configured to be disposed within a groove defined in the proximal shaft portion.

8. The surgical instrument of claim 7, wherein the drive member includes a recessed groove defined within internal walls defining a recessed space.

9. The surgical instrument of claim 8, wherein the proximal shaft portion is configured to be received in the recessed space of the drive member.

10. The surgical instrument of claim 9, wherein when the proximal shaft portion is received in the recessed space of the drive member, wherein the retention ring is configured to compress against the internal walls defining the recessed space until eventual receipt into the recessed groove.

11. The surgical instrument of claim 1, wherein the proximal shaft portion includes a spring disposed on the proximal shaft portion and a resiliently biased clamping component.

12. The surgical instrument of claim 11, wherein the resiliently biased clamping component includes retention arms having end wedges configured to be disposed within a groove defined the drive member.

13. The surgical instrument of claim 12, wherein the end wedges are resiliently biased outward.

14. The surgical instrument of claim 12, wherein when the rotator knob is directed proximally into the distal aperture, wherein the proximal portion of the rotator knob is configured to grip the retention arms of the clamping component and compress the retention arms inwardly until the end wedges of the retention arms are disposed within the groove of the drive member.

15. The surgical instrument of claim 14, wherein the rotator is removable and is configured to be directed distally when the end wedges are disposed within the groove of the drive member such that the proximal portion of the rotator releases the retention arms of the clamping component to allow the retention arms to return to a resiliently biased outward position.

16. A surgical instrument comprising:
(a) a handle assembly comprising:
  i. a trigger,
  ii. a housing having a distal aperture formed in a distal end of the housing,
  iii. a drive member disposed within the housing, wherein the drive member is in communication with the trigger, and
  iv. a biasing member; and
(b) a transmission assembly comprising:
  i. a proximal shaft portion received within the distal aperture,
  ii. a distal shaft assembly extending distally from the proximal shaft portion, the distal shaft assembly comprising an inner tube; and
  iii. an end effector coupled to a distal end of the distal shaft assembly;
wherein the drive member is configured to removably engage the proximal shaft portion of the transmission assembly via the biasing member, and wherein the proximal shaft portion of the transmission assembly is configured to be removed distally from the distal aperture of the housing.

17. The surgical instrument of claim 16,
wherein the biasing member comprises spring loaded ball bearings disposed on a yoke communicating with the drive member and the trigger, and wherein the spring loaded ball bearings are configured for attachment to a notch in the proximal shaft portion; and
wherein a standoff yoke surface is disposed within the yoke, wherein the standoff yoke surface defines an aperture, wherein the aperture is sized to receive a waveguide of the transmission assembly, wherein the standoff yoke surface is disposed to sit flush against a proximal end of the transmission assembly from which the waveguide extends when the drive member is engaged to the transmission assembly such that the standoff yoke surface provides for a high distal pushing force and a corresponding low proximal pulling force against the engaged transmission assembly.

18. The surgical instrument of claim 16, wherein the proximal shaft portion comprises a portion of an inner tube of the transmission assembly, wherein the biasing member comprises ball bearings disposed on the drive member, and wherein the ball bearings are configured for attachment to respective notches in the inner tube.

19. A surgical instrument comprising:
(a) a handle assembly comprising:
  i. a trigger,
  ii. a housing having a distal aperture formed in a distal end of the housing, and
  iv. a drive member in communication with the trigger such that actuation of the trigger is configured to actuate the drive member in a first direction; and
(b) a transmission assembly comprising:
  i. a proximal shaft portion,
  ii. a rotator knob, the rotator knob having a proximal portion, the proximal portion having a coupling feature,
  iii. a distal shaft assembly extending distally relative to the rotator knob, and
  iv. an end effector coupled to a distal end of the distal shaft assembly;
wherein the drive member of the handle assembly is removably coupled to the proximal shaft portion of the transmission assembly,
wherein the coupling feature on the proximal portion of the rotator knob includes tabs configured to abut ledges defining a portion of the distal aperture of the housing when the transmission assembly is removably coupled to the handle assembly.

20. The surgical instrument of claim 19, wherein the tabs are resiliently biased to abut the ledges.

* * * * *